United States Patent
Sato et al.

(10) Patent No.: US 10,018,641 B2
(45) Date of Patent: Jul. 10, 2018

(54) METHOD FOR QUANTIFYING CHOLESTEROL IN HIGH DENSITY LIPOPROTEIN 3

(71) Applicant: DENKA SEIKEN CO., LTD., Tokyo (JP)

(72) Inventors: Noriyuki Sato, Gosen (JP); Yuhko Hirao, Gosen (JP); Yasuki Itoh, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 0 days.

(21) Appl. No.: 14/374,798

(22) PCT Filed: Jan. 24, 2013

(86) PCT No.: PCT/JP2013/051462
§ 371 (c)(1),
(2) Date: Jul. 25, 2014

(87) PCT Pub. No.: WO2013/111820
PCT Pub. Date: Aug. 1, 2013

(65) Prior Publication Data
US 2015/0044774 A1    Feb. 12, 2015

(30) Foreign Application Priority Data
Jan. 25, 2012 (JP) .................. 2012-013145

(51) Int. Cl.
*G01N 33/92* (2006.01)
*C12Q 1/60* (2006.01)
*G01N 33/00* (2006.01)

(52) U.S. Cl.
CPC .............. *G01N 33/92* (2013.01); *C12Q 1/60* (2013.01)

(58) Field of Classification Search
CPC ... C12Q 1/60; C12Q 1/42; C12Q 1/26; G01N 33/92

(Continued)

(56) References Cited

U.S. PATENT DOCUMENTS

| 2008/0124748 A1* | 5/2008 | Matsui et al. ................ 435/11 |
| 2009/0023167 A1* | 1/2009 | Miyauchi ................ C12Q 1/26 435/11 |
| 2009/0226944 A1* | 9/2009 | Katayama ................ C12Q 1/44 435/11 |

FOREIGN PATENT DOCUMENTS

| EP | 2 597 158 A1 | 5/2013 |
| EP | 2 597 468 A1 | 5/2013 |

(Continued)

OTHER PUBLICATIONS

International Search Report (Form PCT/ISA/210) and English translation thereof, dated Mar. 5, 2013, for International Application No. PCT/JP2013/051462.

(Continued)

*Primary Examiner* — Rebecca M Fritchman
(74) *Attorney, Agent, or Firm* — Birch, Stewart, Kolasch & Birch, LLP

(57) ABSTRACT

Disclosed is the provision of a method for quantifying HDL3 in a test sample without requiring a laborious operation. The method for quantifying cholesterol in high-density lipoprotein 3 comprises allowing a surfactant(s) which specifically react(s) with a high-density lipoprotein 3 to react with a test sample and quantifying cholesterol, and the surfactant(s) is(are) at least one selected from the group consisting of polyoxyethylene polycyclic phenyl ether and polyoxyethylene styrenated phenyl ether.

13 Claims, 2 Drawing Sheets

Correlation of HDL3 with Precipitation Method

(58) Field of Classification Search
USPC .............................................. 435/11; 436/71
See application file for complete search history.

(56) References Cited

FOREIGN PATENT DOCUMENTS

JP       2001-346598 A1    12/2001
JP       2009-207463 A     9/2009

OTHER PUBLICATIONS

Kurosaki et al., "Reactivity of a detergent, polyoxyethylene derivative, with high density lipoprotein subclass", Journal of Analytical Bio-Science, vol. 32, No. 5, 2009, pp. 434-439.

Miller et al., "Seven Direct Methods for Measuring HDL and LDL Cholesterol Compared with Ultracentrifugation Reference Measurement Procedures", Clinical Chemistry, vol. 56, No. 6, 2010, pp. 977-986.

Rosenson et al., "HDL Measures, Particle Heterogeneity, Proposed Nomenclature, and Relation to Atherosclerotic Cardiovascular Events", Clinical Chemistry, vol. 57, No. 3, 2011, pp. 392-410.

Written Opinion of the International Searching Authority (Form PCT/ISA/237) and English Translation thereof, dated Mar. 5, 2013, for International Application No. PCT/JP2013/051462.

Extended European Search Report, dated Aug. 12, 2015, for European Application No. 13740877.9.

Ito et al., "Development of a Homogeneous Assay for Measurement of High-density Lipoprotein-subclass Cholesterol," Clinica Chimica Acta, vol. 427, 2014 (Available Online Sep. 19, 2013), pp. 86-93.

Okada et al., "Direct Measurement of HDL Cholesterol: Method Eliminating Apolipoprotein E-Rich Particles," Journal of Clinical Laboratory Analysis, vol. 15, 2001, pp. 223-229, XP-002382300.

Kao Corporation, Product Information Catalog for "EMULGEN", published Oct. 2001 or Oct. 2010 (correct date unknown), pp. 1-6, with partial translation of p. 4 (8 pages total).

Maeda et al., "Associations between Small Dense LDL, HDL Subfractions (HDL2, HDL3) and Risk of Atherosclerosis in Japanese-Americans," Journal of Atherosclerosis and Thrombosis, vol. 19, No. 5, 2012, pp. 444-452.

\* cited by examiner

METHOD FOR QUANTIFYING CHOLESTEROL IN HIGH DENSITY LIPOPROTEIN 3

TECHNICAL FIELD

The present invention relates to a method for quantifying cholesterol in high-density lipoprotein 3 (which may be hereinafter referred to as "HDL3") (cholesterol in HDL3 may be hereinafter referred to as "HDL3 cholesterol" or "HDL3-C").

BACKGROUND ART

Since high-density lipoprotein (HDL) receives cholesterol from various tissues including walls of blood vessels with arteriosclerosis, it is involved in the action of removal of cholesterol accumulated in cells. Therefore, HDL cholesterol is also called the reverse cholesterol transport system. High-density lipoprotein is known to have a negative correlation with arteriosclerotic diseases such as coronary arteriosclerosis. Accordingly, an HDL value lower than a predetermined lower limit is regarded as an indication of dyslipidemia, and the value is known to be useful as an index of arteriosclerosis.

HDL is constituted by apoprotein, phospholipid, cholesterol and triglyceride. HDL has a density of d=1.063 to 1.210 g/mL, and can be divided into two fractions, that is, HDL2 wherein d=1.063 to 1.125 g/mL and HDL3 wherein d=1.125 to 1.210 g/mL. A notch is found at the portion of d=1.125 in the distribution curve of lipoprotein, and the part having higher densities in the curve corresponds to HDL3. Alternatively, HDL can be divided into subfractions based on the difference in the content of apolipoprotein E among apoproteins in HDL, and HDLs having higher contents of apoE are defined as apoE-rich HDL.

In terms of the functions, HDL has been conventionally studied as a whole, but each of the subfractions HDL2 and HDL3 is now known to have unique functions. It is clinically known that CETP deficiency prevents cholesterol transport from HDL to LDL and IDL, leading to an increase in the HDL cholesterol level. The HDL increased by CETP deficiency is HDL2. HDL2 is said to have an antiarteriosclerotic action. It is also said that CETP deficiency causes an increase in apoE-rich HDL, and that, since apoE-rich HDL has a strong cholesterol-drawing ability and antiplatelet action, it is a good HDL. Further, a decrease in the hepatic lipase activity prevents conversion of HDL3 to HDL2, resulting in an increase in HDL3. It is suggested that increased HDL3 leads to increased incidence rates of coronary artery diseases. In view of such tendencies, it is expected that measurement of each HDL subfraction may contribute to judgment of whether or not a patient is suffering from an arteriosclerotic disease and of the cause of the disease. Further, at present, in view of these functions of HDL subfractions, manufacturers are developing therapeutic agents that inhibit the function of CETP, decrease the LDL cholesterol level, and increase the HDL cholesterol level.

Establishment of a simple method for measuring the HDL subfractions may lead to detailed elucidation of their functions, and to their therapeutic effects in the future.

Examples of methods for measuring HDL subfractions which have been known so far include ultracentrifugation, high-performance liquid chromatography (HPLC), HDL3 precipitation (Patent Document 1) and NMR.

In ultracentrifugation, fractionation is carried out by centrifugation utilizing the difference in the density of lipoprotein. This method has drawbacks in that the operation requires a skill; the method takes many days; and the cost is high. In the method by Okazaki et al. wherein HPLC is used for separating HDL2 and HDL3, the operation takes a long time, and special equipment is required. HDL3 precipitation is a method wherein a reagent containing a divalent metal ion and dextran sulfate is used to aggregate lipoproteins other than HDL3, and HDL3 in the supernatant portion is recovered by centrifugation and measured using an automatic analyzer. This method is not widely used since the method has drawbacks in that the operation of this method also requires a skill; the method is a manual method; the method requires an operation of sample pretreatment; and a certain length of time is required before measurement. Further, NMR, which is a method wherein the number of particles of lipoprotein is measured by magnetic resonance, is not commonly employed since the method requires special equipment.

There is another method for analyzing an HDL subfraction (Patent Document 2). Although this method enables measurement with a general purpose automatic analyzer, the method employs a method wherein a surfactant is used to prevent an enzyme from acting on lipoproteins other than HDL3. Therefore, since the HDL3 reaction is allowed to proceed in the presence of the lipoproteins other than the lipoprotein of interest, the measurement might be influenced by such lipoproteins or, in cases where the prevention is not sufficient, the lipoproteins other than HDL3 might be undesirably measured together.

Thus, as an alternative to the above methods, a reagent which enables simple and more selective quantification of the cholesterol level needs to be invented.

PRIOR ART DOCUMENTS

Patent Documents

[Patent Document 1] JP 2009-207463 A
[Patent Document 2] JP 2001-346598 A

SUMMARY OF THE INVENTION

Problems to be Solved by the Invention

An object of the present invention is to provide a method for quantifying HDL3 in a test sample without requiring a laborious operation.

Means for Solving the Problems

The present inventors intensively studied to discover a surfactant(s) which specifically react(s) with HDL3. The present inventors then inferred that HDL3 cholesterol in a test sample can be quantified by allowing such a surfactant(s) to react with a test sample and quantifying cholesterol, and confirmed that this is possible, thereby completing the present invention.

That is, the present invention provides a method for quantifying cholesterol in high-density lipoprotein 3, the method comprising allowing a surfactant(s) which specifically react(s) with high-density lipoprotein 3 to react with a test sample and quantifying cholesterol, which surfactant(s) is(are) at least one selected from the group consisting of polyoxyethylene polycyclic phenyl ether and polyoxyethylene styrenated phenyl ether.

Effect of the Invention

By the present invention, HDL3 cholesterol in a test sample can be specifically quantified with an automatic analyzer without requiring a laborious operation such as ultracentrifugation or pretreatment. Further, quantification of the HDL2 cholesterol level can also be carried out by subtracting the HDL3 cholesterol level from the total HDL cholesterol level obtained by a conventional method for quantifying the total HDL cholesterol in a test sample.

MODE FOR CARRYING OUT THE INVENTION

Figure 1:
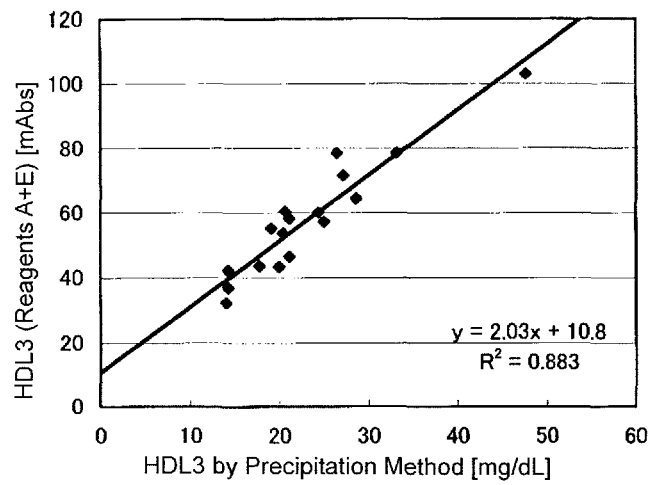
FIG. 1 shows a diagram illustrating a correlation between HDL3 cholesterol level determined by the present invention and HDL3 cholesterol level determined by precipitation method, which comparison was carried out in Example 3.

The test sample to be subjected to the method of the present invention is not restricted as long as HDL3 cholesterol in the sample can be quantified, and the test sample is preferably serum or blood plasma, or a dilution thereof. Serum or a dilution thereof is especially preferred.

In the method of the present invention, a surfactant(s) which specifically react(s) with HDL3 (which means that the surfactant hardly reacts with lipoproteins other than HDL3) is(are) reacted with a test sample. The surfactant(s) which specifically react(s) with HDL3 is(are) at least one selected from the group consisting of polyoxyethylene styrenated phenyl ether and polyoxyethylene polycyclic phenyl ether.

More specifically, examples of polyoxyethylene polycyclic phenyl ether include Newcol-610 (Trade name, produced by Nippon Nyukazai Co., Ltd., company names hereinafter represent names of manufacturers, and all names described together with company names hereinafter represent trade names) and Newcol-710 (Nippon Nyukazai); and examples of polyoxyethylene styrenated phenyl ether include ADEKATOL PC-10 (ADEKA), BLAUNON DSP-12.5 (AOKI OIL INDUSTRIAL), BLAUNON TSP-16 (AOKI OIL INDUSTRIAL), Noigen EA-137 (Dai-ichi Kogyo Seiyaku) and Noigen EA-157 (Dai-ichi Kogyo Seiyaku). Each of these surfactants may be used alone, or two or more types of the surfactants may be used in combination.

When the term "react" is used for a surfactant in the present invention, the term means that the surfactant leads lipoprotein to the outside of the reaction system, making an enzyme act easily, or means to protect lipoprotein such that an enzyme cannot act on the lipoprotein.

The concentration of the surfactant is preferably 0.01 to 5.0% (w/v), more preferably 0.05 to 3.0% (w/v).

In the method of the present invention, cholesterol is quantified by the reaction of the above surfactants. Methods of quantification per se of cholesterol are well known, and any of the well-known methods may be used. A concrete description is also given in Examples below. For example, ester-type cholesterol in lipoprotein is hydrolyzed with cholesterol esterase to produce free cholesterol and a fatty acid, and the produced free cholesterol and free cholesterol inherently existing in lipoprotein are converted using cholesterol oxidase to generate cholestenone and hydrogen peroxide. A quinone pigment is then formed in the presence of peroxidase, and quantified. Examples of compounds that generate a quinone pigment include HDAOS (N-(2-hydroxy-3-sulfopropyl)-3,5-dimethoxyaniline), DAOS (N-ethyl-N-(2-hydroxy-3-sulfopropyl)-3,5-dimethoxyaniline sodium salt) or TOOS (N-ethyl-N-(2-hydroxy-3-sulfopropyl)-3-methylaniline sodium salt dihydrate) and 4-aminoantipyrine, but the compounds are not restricted as long as the combination allows generation of a quinone pigment. In cases where cholesterol esterase and cholesterol oxidase are used in the preceding step described later, the cholesterol esterase and cholesterol oxidase used in the preceding step may be used as they are in the step of the present invention (step of reacting an HDL3-specific surfactant), without further addition.

The concentration of the compound for generation of a quinone pigment is, for example, preferably about 0.5 to about 3.0 mmol/L in the case of TOOS, or 0.1 to 2.0 mmol/L in the case of 4-aminoantipyrine. The concentration of peroxidase is preferably 0.4 to 5.0 U/mL.

As the reaction liquid, various buffers used in normal biochemical reactions may be used, and the pH of the reaction liquid is preferably between 5 and 8. The solution is preferably Good's, Tris, phosphate or glycine buffer solution, and is preferably a Good's buffer such as bis(2-hydroxyethyl)iminotris(hydroxyethyl)methane(Bis-Tris), piperazine-1,4-bis(2-ethanesulfonic acid) (PIPES), piperazine-1,4-bis(2-ethanesulfonic acid), sesqui sodium salt monohydrate (PIPES 1.5Na), 2-hydroxy-3-morpholinopropanesulfonic acid (MOPSO), N,N-bis(2-hydroxyethyl)-2-aminoethanesulfonic acid (BES), 2-[4-(2-hydroxyethyl)-1-piperazinyl]ethanesulfonic acid (HEPES) or piperazine-1,4-bis(2-hydroxy-3-propanesulfonic acid) (POPSO).

The reaction temperature is preferably about 25 to about 40° C., more preferably 35 to 38° C., most preferably 37° C. The reaction time is not restricted, and is usually about 2 to about 10 minutes.

The method of the present invention can also be carried out by directly reacting the surfactant with the test sample, but is preferably carried out by first performing the preceding step for transferring cholesterol in lipoproteins other than HDL or HDL3 to the outside of the reaction system and then subjecting the sample after the preceding step to the method of the present invention, in view of more accurate quantification of HDL3 cholesterol.

The preceding step is preferably carried out in the presence of a surfactant that reacts with lipoproteins other than HDL or a surfactant that reacts with lipoproteins other than HDL3.

Examples of the surfactant that reacts with lipoproteins other than HDL or HDL3 include, but are not limited to, nonionic surfactants such as polyoxyethylene sorbitan derivatives, polyoxyethylene-polyoxypropylene condensates and polyoxyethylene-stearylamine; anionic surfactants such as amide ether sulfate and polyoxyethylene alkyl ether sodium sulfate; amphoteric surfactants such as coconut oil fatty acid-amidopropyldimethyl-aminoacetic acid betaine, alkyl dimethyl-aminoacetic acid betaine and lauryl betaine; and cationic surfactants such as lauryl trimethyl ammonium chloride.

More specifically, Examples of the surfactant that reacts with lipoproteins other than HDL or HDL3 include nonionic surfactants such as polyoxyethylene sorbitan monooleate Nonion OT-221 (NOF Corporation), polyoxyethylene-polyoxypropylene condensate Pluronic F68 (ADEKA), Pluronic F88 (ADEKA), Pluronic F127 (ADEKA), Pluronic P103 (ADEKA), Pluronic P123 (ADEKA), polyoxyethylene-stearylamine Nymeen S210 (NOF Corporation), Emulgen A500 (Kao Corporation); anionic surfactants such as amide ether sulfate Sunamide CF-10 (NOF Corporation), polyoxyethylene alkyl ether sodium sulfate Levenol WX (Kao Corporation); amphoteric surfactants such as coconut oil fatty acid-amidopropyldimethyl-aminoacetic acid betaine Nissan Anon BDF-SF (NOF Corporation), alkyl dimethyl-aminoacetic acid betaine Nissan Anon BF (NOF Corporation) and lauryl betaine Amphitol 24B (Kao Corporation); and cationic surfactants such as lauryl trimethyl ammonium chloride Kohtamin 24P (Kao Corporation). Each of these may be used alone, or two or more types of these may be used in combination.

The concentration of the surfactant to be used in the preceding step is preferably 0.01 to 5.0% (w/v), more preferably about 0.03 to about 3.0% (w/v).

In the preceding step, cholesterol is transferred to the outside of the reaction system by the reaction with the surfactant. The term "transferred to the outside of the reaction system" herein means that cholesterol and esters thereof are eliminated or protected such that the cholesterol and esters thereof are not involved in the later steps.

The term "elimination" herein means that cholesterol of lipoprotein in a test sample is degraded such that the cholesterol does not affect the reaction for measurement of cholesterol in a later step. Examples of the method for eliminating lipoprotein cholesterol include a method wherein cholesterol esterase and cholesterol oxidase are allowed to act on the cholesterol, followed by decomposition of the produced hydrogen peroxide into water and oxygen using catalase. Alternatively, a hydrogen donor may be reacted with the produced hydrogen peroxide using peroxidase to convert the hydrogen peroxide to a colorless quinone. The method for eliminating lipoprotein cholesterol is not restricted to these. The method of elimination of cholesterol per se is well known in the art, and is also described concretely in Examples below.

The term "protection" means to protect lipoprotein in a test sample such that the lipoprotein does not react upon cholesterol measurement in a later step. Examples of the method of protection of lipoprotein include, but are not limited to, a method wherein a surfactant is used to specifically protect each lipoprotein such that cholesterol esterase and cholesterol oxidase do not act on the lipoprotein.

In cases where the preceding step wherein hydrogen peroxide produced in the preceding step is decomposed using catalase is used, a catalase inhibitor sodium azide is used by addition to the reaction liquid in the second step. The concentration of sodium azide in this case is usually about 0.1 g/L to about 1.0 g/L.

The present inventors further discovered that phospholipase and sphingomyelinase act on lipoproteins but hardly act on HDL3. Accordingly, by allowing phospholipase and/or sphingomyelinase (these may be hereinafter collectively referred to as the "phospholipase and/or the like") to coexist with the above-described surfactant, HDL3 cholesterol can be more accurately quantified, which is preferred.

The phospholipase is not restricted as long as it acts on phosphatidyl choline. Phospholipase A, phospholipase C and phospholipase D are preferred, and phospholipase C and phospholipase D are especially preferred. The sphingomyelinase is not restricted as long as it acts on sphingomyelin. Since the phospholipase and/or the like are commercially available, commercially available products may be preferably used. Each of the phospholipase and/or the like may be used alone, or two or more types of the phospholipase and the like may be used in combination.

The final concentration of phospholipase and/or the like (the total concentration, in cases where two or more types of phospholipase are used in combination) is preferably about 0.1 to about 100 U/mL, more preferably about 0.2 to about 50 U/mL.

Also in cases where the preceding step is carried out in the presence of a surfactant, the reaction conditions (reaction temperature, time, buffer and the like) are as described above.

In the preceding step, the reaction step by an enzyme and the reaction step by a surfactant can be carried out simultaneously as a single step by simultaneously adding an enzyme system and surfactant for transferring cholesterol to the outside of the reaction system. Different surfactants are used between the first step and the second step.

In cases where cholesterol esterase and cholesterol oxidase are used in the preceding step, the concentration of cholesterol esterase is preferably about 0.1 to about 10.0 U/mL, more preferably about 0.2 to about 3.0 U/mL. The concentration of cholesterol oxidase is preferably about 0.05 to about 10.0 U/mL, more preferably about 0.1 to about 1.0 U/mL. The cholesterol esterase is not restricted as long as it acts on ester-type cholesterol, and examples of the cholesterol esterase which may be used include commercially available products such as cholesterol esterase (CEBP) manufactured by Asahi Kasei Corporation and cholesterol esterase (COE-311, COE-312) manufactured by Toyobo Co., Ltd. Further, the cholesterol oxidase is not restricted as long as it acts on free cholesterol, and examples of the cholesterol oxidase which may be used include commercially available products such as cholesterol oxidase (CONII) manufactured by Asahi Kasei Corporation and cholesterol oxidase (COO-311, COO-321, COO-331) manufactured by Toyobo Co., Ltd.

In cases where peroxidase is used in the preceding step, the concentration of peroxidase is preferably about 2.0 to about 5.0 U/mL, more preferably about 3.0 to about 4.0 U/mL. In cases where a compound for conversion into a colorless quinone is used, the concentration of the compound is preferably about 0.4 to about 0.8 mmol/L.

The other conditions for the preceding step (reaction temperature, reaction time, buffer and the like) may be the same as that for the above-described method of the present invention.

The present invention will now be described more concretely by way of Examples below. However, the present invention is not limited to the Examples below.

EXAMPLES

Example 1

Fractionation was carried out to obtain the HDL2 fraction and the HDL3 fraction as follows. A test sample containing HDL, that is, serum was subjected to ultracentrifugation using a solution with sodium chloride and sodium bromide such that separation occurs at a density at the border between HDL2 and HDL3 (1.125), and each resulting fraction was collected.

Fractionation by ultracentrifugation was carried out to obtain the CM-VLDL fraction, LDL fraction, HDL2 fraction and HDL3 fraction, and each fraction was reacted with Reagent A described below. Reagent B described below was further added to the reaction solution to perform measurement. In the measurement, 150 µL of Reagent A was added to 2 µL of each fraction, and the reaction was allowed to proceed for 5 minutes with warming, followed by addition of 50 µL of Reagent B to the reaction solution and additional 5 minutes of reaction with warming. The absorbances at a main wavelength of 600 nm and a sub-wavelength of 700 nm were measured.

| Reagent A | |
|---|---|
| BES buffer (pH 6.6) | 100 mmol/L |
| TOOS | 1.5 mmol/L |
| Pluronic F88 | 0.05 w/v % |
| Catalase | 600 U/mL |
| Cholesterol oxidase | 0.8 U/mL |
| Cholesterol esterase | 2.0 U/mL |
| Sphingomyelinase | 0.5 U/mL |

| Reagent B | |
|---|---|
| BES buffer (pH 7.0) | 100 mmol/L |
| Sodium azide | 0.1% |
| Various surfactants* | 2.0 w/v % |
| 4-Aminoantipyrine | 4.0 mmol/L |
| Peroxidase | 3.5 U/mL |

*In cases where two or more surfactants are used in combination, the total amount is 2.0 w/v %.

The amount of the change in absorbance of each fraction at a unit time after the addition of Reagent B is shown in Table 1. Specific reaction with HDL3 can be confirmed.

TABLE 1

| | CM-VLDL | LDL | HDL2 | HDL3 |
|---|---|---|---|---|
| Newcol-610 | 1.9 | 1.0 | 13.5 | 38.2 |
| Newcol-710 | 0.7 | 1.5 | 9.4 | 30.5 |
| Mixture of Noigen EA-137 and Noigen EA-157 | 1.5 | 1.4 | 23.9 | 47.0 |

(unit: mAbs)

Example 2

Fractionation by ultracentrifugation was carried out to obtain the CM-VLDL fraction, LDL fraction, HDL2 fraction and HDL3 fraction, and each fraction was reacted with Reagent C described below. Reagent D described below was further added to the reaction solution to perform measurement. In the measurement, 150 µL of Reagent C was added to 2 µL of each fraction, and the reaction was allowed to proceed for 5 minutes with warming, followed by addition of 50 µL of Reagent D to the reaction solution and additional 5 minutes of reaction with warming. The absorbances at a main wavelength of 600 nm and a sub-wavelength of 700 nm were measured.

| Reagent C | |
|---|---|
| BES buffer (pH 6.6) | 100 mmol/L |
| HDAOS | 0.56 mmol/L |
| Nonion OT-221 | 0.01 w/v % |
| Catalase | 600 U/mL |
| Cholesterol oxidase | 0.8 U/mL |
| Cholesterol esterase | 2.8 U/mL |

| Reagent D | |
|---|---|
| BES buffer (pH 7.0) | 100 mmol/L |
| Sodium azide | 0.1% |
| Newcol-610 | 2.0 w/v % |
| 4-Aminoantipyrine | 4.0 mmol/L |
| Peroxidase | 3.5 U/mL |

The amount of the change in absorbance of each fraction at a unit time after the addition of Reagent D is shown in Table 2. Specific reaction with HDL3 can be confirmed.

TABLE 2

| | CM-VLDL | LDL | HDL2 | HDL3 |
|---|---|---|---|---|
| Newcol-610 | 0.9 | 2.0 | 1.3 | 50.4 |

(unit: mAbs)

Example 3

A human serum sample was reacted with Reagent A described above, and Reagent E described below was further added to the reaction solution to perform measurement. In the measurement, 150 µL of Reagent A was added to 2 µL of serum, and the reaction was allowed to proceed for 5 minutes with warming, followed by addition of 50 µL of Reagent E to the reaction solution and additional unit time of reaction with warming. The absorbances at a main wavelength of 600 nm and a sub-wavelength of 700 nm were measured to determine HDL3 cholesterol level, and HDL2 cholesterol level was determined by calculation based on the total HDL cholesterol measured otherwise.

| Reagent E | |
|---|---|
| BES buffer (pH 7.0) | 100 mmol/L |
| Sodium azide | 0.1% |
| Newcol-710 | 2.0 w/v % |
| 4-Aminoantipyrine | 4.0 mmol/L |
| Peroxidase | 3.5 U/mL |

Figure 2:
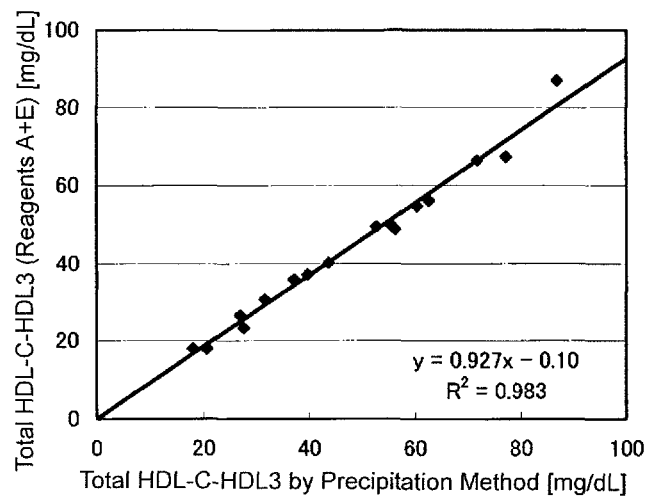
FIG. 2 shows a diagram illustrating a correlation between HDL2 cholesterol level calculated from HDL3 cholesterol level determined by the present invention and the total HDL cholesterol level, and HDL2 cholesterol level calculated from HDL3 cholesterol level determined by precipitation method and the total cholesterol level, which comparison was carried out in Example 3.

The correlation between HDL3 cholesterol level determined by using Reagent A and Reagent E and HDL3 cholesterol level determined by precipitation method (Patent Document 1) is shown in FIG. 1. The correlation between HDL2 cholesterol level calculated from HDL3 cholesterol level determined by using Reagent A and Reagent E and the total HDL cholesterol level, and HDL2 cholesterol level calculated from HDL3 cholesterol level determined by precipitation method and the total HDL cholesterol level, is shown in FIG. 2. For both HDL3 and HDL2, strong correlations can be confirmed between the method of the present invention and the precipitation method.

Example 4

A human serum sample was reacted with Reagent F described below, and Reagent E described above was further added to the reaction solution to perform measurement. In the measurement, 150 μL of Reagent F was added to 2 μL of serum, and the reaction was allowed to proceed for 5 minutes with warming, followed by addition of 50 μL of Reagent E to the reaction solution and additional unit time of reaction with warming. The absorbances at a main wavelength of 600 nm and a sub-wavelength of 700 nm were measured to determine HDL3 cholesterol level, and HDL2 cholesterol level was determined by calculation based on the total HDL cholesterol measured otherwise.

| Reagent F | |
|---|---|
| BES buffer (pH 6.6) | 100 mmol/L |
| HDAOS | 0.56 mmol/L |
| Nonion OT-221 | 0.01 w/v % |
| Catalase | 600 U/mL |
| Cholesterol oxidase | 0.8 U/mL |
| Cholesterol esterase | 2.0 U/mL |
| Sphingomyelinase | 0.5 U/mL |

Figure 3:
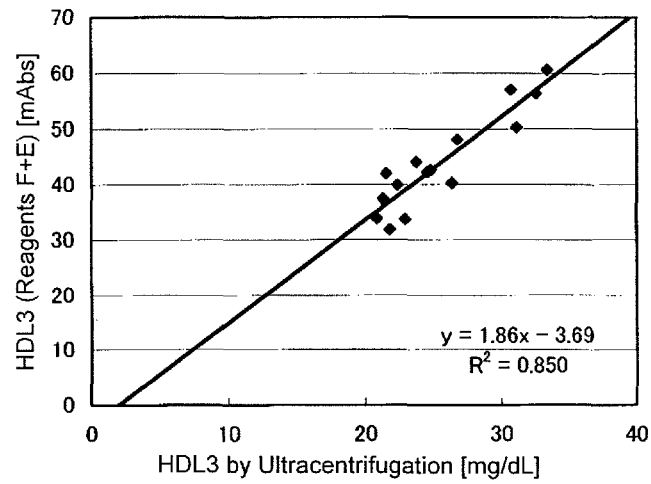
FIG. 3 shows a diagram illustrating a correlation between HDL3 cholesterol level determined by the present invention and HDL3 cholesterol level determined by ultracentrifugation, which comparison was carried out in Example 4.
Figure 4:
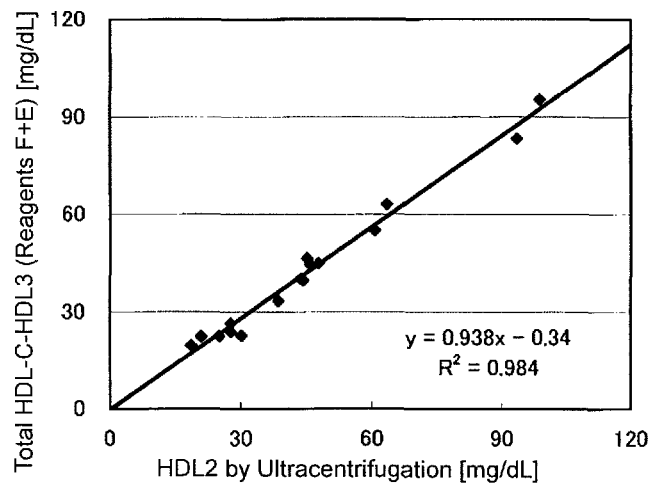
FIG. 4 shows a diagram illustrating a correlation between HDL2 cholesterol level calculated from HDL3 cholesterol level determined by the present invention and the total HDL cholesterol, and HDL2 cholesterol level determined by ultracentrifugation, which comparison was carried out in Example 4.

The correlation between HDL3 cholesterol level determined by using Reagent F and Reagent E and HDL3 cholesterol level determined by ultracentrifugation is shown in FIG. 3. The correlation between HDL2 cholesterol level calculated from HDL3 cholesterol level determined by using Reagent F and Reagent E and the total HDL cholesterol level, and HDL2 cholesterol level determined by ultracentrifugation is shown in FIG. 4. For both HDL3 and HDL2, strong correlations can be confirmed between the method of the present invention and the ultracentrifugation.

The invention claimed is:

1. A method for quantifying cholesterol in high-density lipoprotein 3 in a test sample from a human patient, said method comprising:
    obtaining the test sample of serum or blood plasma containing high-density lipoprotein 3 from the human patient;
    adding a surfactant(s) selected from the group consisting of polyoxyethylene polycyclic phenyl ether and polyoxyethylene styrenated phenyl ether to the test sample or a dilution thereof at a surfactant concentration of 0.01 to 5.0% w/v to selectively solubilize high-density lipoprotein 3 and release the cholesterol therefrom; and
    quantifying the cholesterol in the high-density lipoprotein 3 of the test sample by optically measuring the cholesterol released from the selectively solubilized high-density lipoprotein 3,
    wherein high-density lipoprotein 2 is not selectively solubilized by the addition of the surfactant(s) and high-density lipoprotein 2 cholesterol is not included in the quantification of the cholesterol.

2. The method of claim 1, wherein the polyoxyethylene polycyclic phenyl ether is selected from the group consisting of Newcol-610 and Newcol-710.

3. The method of claim 1, wherein the polyoxyethylene styrenated phenyl ether is selected from the group consisting of ADEKATOL PC-10, BLAUNON DSP-12.5, BLAUNON TSP-16, Noigen EA-137, and Noigen EA-157.

4. The method of claim 1, wherein the released cholesterol is optically measured via a cholesterol esterase, cholesterol oxidase, and a quinone pigment.

5. The method of claim 1, wherein the concentration of the surfactant is 0.05 to 3.0% w/v.

6. A method for quantifying cholesterol in high-density lipoprotein 3, comprising:
    protecting and/or eliminating cholesterol in lipoproteins other than HDL or HDL3, and allowing a surfactant to selectively solubilize high-density lipoprotein 3 releasing the cholesterol from the high-density lipoprotein 3 into the test sample and quantifying the released cholesterol,
    wherein high-density lipoprotein 2 is not selectively solubilized by the addition of the surfactant and high-density lipoprotein 2 cholesterol is not included in the quantified cholesterol,
    wherein the surfactant that selectively solubilizes high-density lipoprotein 3 is selected from the group consisting of polyoxyethylene polycyclic phenyl ether and polyoxyethylene styrenated phenyl ether,
    wherein the protecting and/or eliminating cholesterol in lipoproteins other than HDL or HDL3 is carried out in the presence of a surfactant that reacts with lipoproteins other than HDL.

7. The method of claim 6, wherein the surfactant that reacts with lipoproteins other than HDL comprises polyoxyethylene sorbitan derivatives, polyoxyethylene-polyoxypropylene condensates, polyoxyethylene-stearylamine, anionic surfactants, amphoteric surfactants, and cationic surfactants.

8. A method for quantifying cholesterol in high-density lipoprotein 3, said method comprising:
    allowing a surfactant(s) which react(s) with high-density lipoprotein 3 to react with a test sample; and
    quantifying cholesterol optically, which surfactant(s) is(are) at least one selected from the group consisting of polyoxyethylene polycyclic phenyl ether and polyoxyethylene styrenated phenyl ether,
    wherein high-density lipoprotein 2 is not included in the quantified cholesterol.

9. The method of claim 1, wherein prior to said adding step, cholesterol in lipoproteins other than HDL or HDL3 is protected and/or eliminated.

10. The method of claim 1, wherein cholesterol is quantified by measuring absorbance of light.

11. The method of claim 7, wherein the anionic surfactant is an amide ether sulfate or polyoxyethylene alkyl ether sodium sulfate.

12. The method of claim 7, wherein the amphoteric surfactant is coconut oil fatty acid-amidopropyldimethyl-aminoacetic acid betaine, alkyl dimethyl-aminoacetic acid betaine or lauryl betaine.

13. The method of claim 7, wherein the amphoteric surfactant cationic surfactant is lauryl trimethyl ammonium chloride.

* * * * *